(12) United States Patent
Ahner et al.

(10) Patent No.: US 9,274,064 B2
(45) Date of Patent: Mar. 1, 2016

(54) SURFACE FEATURE MANAGER

(71) Applicant: SEAGATE TECHNOLOGY LLC, Cupertino, CA (US)

(72) Inventors: Joachim Walter Ahner, Livermore, CA (US); David M. Tung, Livermore, CA (US)

(73) Assignee: Seagate Technology LLC, Cupertino, CA (US)

( * ) Notice: Subject to any disclaimer, the term of this patent is extended or adjusted under 35 U.S.C. 154(b) by 0 days.

(21) Appl. No.: 14/194,417

(22) Filed: Feb. 28, 2014

(65) Prior Publication Data

US 2014/0354981 A1 Dec. 4, 2014

Related U.S. Application Data

(60) Provisional application No. 61/829,131, filed on May 30, 2013.

(51) Int. Cl.
*G01N 21/00* (2006.01)
*G01N 21/95* (2006.01)

(52) U.S. Cl.
CPC ...................................... *G01N 21/95* (2013.01)

(58) Field of Classification Search
CPC ............ G01N 21/9501; G01N 21/956; G01N 2021/4711; G01N 2021/473; G01N 2021/8861; G01N 2021/8864; G01N 2021/95676; G01N 21/65; G01N 21/9505; G01N 21/8851; G01N 21/94; G01N 21/95; G01N 2223/611

See application file for complete search history.

(56) References Cited

U.S. PATENT DOCUMENTS

| | | |
|---|---|---|
| 4,207,467 A | 6/1980 | Doyle |
| 4,477,890 A | 10/1984 | Cheshkovsky et al. |
| 4,551,919 A | 11/1985 | Sakata et al. |
| 4,598,997 A | 7/1986 | Auderset et al. |
| 4,618,773 A | 10/1986 | Drukier |
| 4,794,550 A | 12/1988 | Greivenkamp |
| 4,806,776 A | 2/1989 | Kley |

(Continued)

FOREIGN PATENT DOCUMENTS

| | | |
|---|---|---|
| JP | 06-241758 A | 9/1994 |
| JP | 08-075661 A | 3/1996 |

(Continued)

OTHER PUBLICATIONS

Candela CS10, Optical X-BeamTM Surface Analyzer, Product Description (www.klatencor.com/defect-inspection/candela-cs10.html), accessed Apr. 17, 2013.

(Continued)

*Primary Examiner* — Michael P Stafira (57) ABSTRACT

Provided herein is an apparatus, including a mapping means for generating a map of locations of surface features of an article based on photon-detector signals corresponding to photons scattered from the surface features of the article, and a surface feature manager. The surface manager is configured to locate a predetermined surface feature of the surface features of the article based, at least in part, on the map of the surface features locations, irradiate photons of a first power onto the location of the predetermined surface feature to analyze the predetermined surface feature, and irradiate photons of a second power onto the location of the predetermined surface feature to remove the predetermined surface feature.

20 Claims, 8 Drawing Sheets

(56) References Cited

U.S. PATENT DOCUMENTS

| | | | |
|---|---|---|---|
| 4,975,571 A | 12/1990 | McMurtry et al. |
| 5,058,178 A | 10/1991 | Ray |
| 5,066,130 A | 11/1991 | Tsukiji et al. |
| 5,131,755 A | 7/1992 | Chadwick et al. |
| 5,168,322 A | 12/1992 | Clarke et al. |
| 5,455,870 A | 10/1995 | Sepai et al. |
| 5,610,392 A | 3/1997 | Nagayama et al. |
| 5,627,638 A | 5/1997 | Vokhmin |
| 5,661,559 A | 8/1997 | Brezoczky et al. |
| 5,726,455 A | 3/1998 | Vurens |
| 5,737,072 A | 4/1998 | Emery et al. |
| 5,774,212 A | 6/1998 | Corby, Jr. |
| 5,778,039 A | 7/1998 | Hossain et al. |
| 5,781,649 A | 7/1998 | Brezoczky |
| 5,859,698 A | 1/1999 | Chau et al. |
| 5,898,491 A | 4/1999 | Horai et al. |
| 5,933,236 A | 8/1999 | Sommargren |
| 5,973,839 A | 10/1999 | Dorsel |
| 6,256,097 B1 | 7/2001 | Wagner |
| 6,392,745 B1 | 5/2002 | Mavliev et al. |
| 6,449,036 B1 | 9/2002 | Wollmann et al. |
| 6,476,908 B1 | 11/2002 | Watson |
| 6,483,584 B1 | 11/2002 | Lee et al. |
| 6,509,966 B2 | 1/2003 | Ishiguro |
| 6,515,742 B1* | 2/2003 | Ruprecht ............... 356/237.4 |
| 6,529,270 B1 | 3/2003 | Bills |
| 6,542,248 B1 | 4/2003 | Schwarz |
| 6,556,783 B1 | 4/2003 | Gelphman |
| 6,559,458 B2 | 5/2003 | Rinn |
| 6,559,926 B2 | 5/2003 | Yamaguchi et al. |
| 6,617,087 B1 | 9/2003 | Rangarajan et al. |
| 6,617,603 B2 | 9/2003 | Ishiguro et al. |
| 6,809,809 B2 | 10/2004 | Kinney et al. |
| 6,819,423 B2 | 11/2004 | Stehle et al. |
| 6,822,734 B1 | 11/2004 | Eidelman et al. |
| 6,847,907 B1* | 1/2005 | Novotny ........................ 702/84 |
| 7,207,862 B2 | 4/2007 | Nabeya et al. |
| 7,433,031 B2 | 10/2008 | Xu et al. |
| 7,474,410 B2 | 1/2009 | Moon |
| 7,489,399 B1 | 2/2009 | Lee |
| 7,684,057 B2 | 3/2010 | Sakai |
| 7,751,609 B1 | 7/2010 | Berman |
| 7,777,876 B2 | 8/2010 | Horai et al. |
| 7,969,567 B2 | 6/2011 | Yoshida et al. |
| 8,018,585 B2 | 9/2011 | Hariyama |
| 8,077,305 B2 | 12/2011 | Owen et al. |
| 8,139,232 B2 | 3/2012 | Wolf et al. |
| 8,223,326 B2 | 7/2012 | Kim et al. |
| 8,294,890 B2 | 10/2012 | Usuda |
| 8,547,545 B2 | 10/2013 | Sasazawa et al. |
| 2001/0036588 A1 | 11/2001 | Buschbeck et al. |
| 2002/0088952 A1 | 7/2002 | Rao et al. |
| 2004/0207836 A1 | 10/2004 | Chhibber et al. |
| 2004/0231177 A1 | 11/2004 | Mies |
| 2005/0067740 A1* | 3/2005 | Haubensak .................. 264/400 |
| 2005/0099204 A1 | 5/2005 | Uh et al. |
| 2005/0174575 A1 | 8/2005 | Norton et al. |
| 2005/0280808 A1 | 12/2005 | Backhauss et al. |
| 2006/0126062 A1 | 6/2006 | Tuschel |
| 2006/0147814 A1* | 7/2006 | Liang ................................ 430/5 |
| 2006/0181700 A1 | 8/2006 | Andrews et al. |
| 2007/0229852 A1 | 10/2007 | Wack et al. |
| 2008/0174771 A1 | 7/2008 | Yan et al. |
| 2008/0309927 A1 | 12/2008 | Grueneberg |
| 2009/0009753 A1 | 1/2009 | Horai et al. |
| 2009/0122304 A1 | 5/2009 | Jin et al. |
| 2009/0320051 A1 | 12/2009 | Meerwald et al. |
| 2009/0323051 A1 | 12/2009 | Matsui |
| 2010/0053602 A1 | 3/2010 | Hayashi et al. |
| 2010/0053603 A1 | 3/2010 | Sakaguchi et al. |
| 2010/0091272 A1 | 4/2010 | Asada et al. |
| 2011/0141272 A1 | 6/2011 | Uto et al. |
| 2012/0140211 A1 | 6/2012 | Oshima et al. |
| 2012/0194808 A1 | 8/2012 | Oka et al. |
| 2013/0077159 A1 | 3/2013 | Tani |
| 2013/0198697 A1* | 8/2013 | Hotzel ............................ 716/51 |
| 2013/0301040 A1 | 11/2013 | Ahner et al. |
| 2014/0043621 A1 | 2/2014 | Ahner et al. |
| 2014/0098364 A1 | 4/2014 | Ahner et al. |
| 2014/0098368 A1 | 4/2014 | Ahner et al. |
| 2014/0104604 A1 | 4/2014 | Ahner et al. |
| 2014/0129179 A1 | 5/2014 | Xu et al. |
| 2014/0160481 A1 | 6/2014 | Ahner et al. |
| 2014/0354980 A1 | 12/2014 | Tung et al. |
| 2014/0354982 A1 | 12/2014 | Ahner et al. |
| 2014/0354984 A1 | 12/2014 | Tung et al. |
| 2014/0354994 A1 | 12/2014 | Ahner et al. |

FOREIGN PATENT DOCUMENTS

| | | |
|---|---|---|
| JP | 08-178867 A | 7/1996 |
| JP | 2003-202214 | 7/2003 |
| JP | 3692685 B2 | 9/2005 |
| JP | 2006-30851 A | 11/2009 |
| JP | 2011-163872 A | 8/2011 |
| JP | 2012-026862 A | 2/2012 |
| JP | 2012-185121 A | 9/2012 |
| KR | 10-0763942 B1 | 10/2007 |
| KR | 10-2011-0021304 A | 3/2011 |
| WO | 96-05503 A1 | 2/1996 |

OTHER PUBLICATIONS

Candela CS20, Advanced Inspection for Compound Semiconductor and Optoelectronic Materials, Optical Surface Analyzer, KLA-Tencor Corporation, 2010.
High-sensitivity, High-speed Dark-field Wafer-defect Inspection System—IS3000, Hitachi Review vol. 55, No. 2, pp. 73-77, Hitachi Ltd., 2003.
Hitachi High-Technologies I-5320 / I-6300—Electron Beam Wafer Inspection System, (www.etesters.com/listing/ea101bfb-1422-08df-aaae-08c275a8ee86/I-5320_-_I-6300_-_Electron_Beam_Wafer_Inspection_System), accessed Jun. 19, 2013.
Hitachi High-Technologies IS3000—Dark Field Wafer Defect Inspection System, (www.etesters.com/listing/ea1312b5-1422-08df-aa4b-5fea5982b63b/IS3000_-_Dark_Field_Wafer_Defect_Inspection_System), accessed Jun. 19, 2013.
Hitachi High-Technologies LS6800—Wafer Surface Inspection System, (www.etesters.com/listing/ea1133d4-1422-08df-aad9-258baeaf6c16/LS6800_-_Wafer_Surfce_Inspection_System), accessed Jun. 19, 2103.
LS Unpatterned Wafer Inspection System, (hitachi-htc.ca/products/sennicondutor-metrology-equipment/inspections-systems/wafer-inspection-system/ls-unpatterne), accessed Jun. 19, 2013.

* cited by examiner

SURFACE FEATURE MANAGER

CROSS REFERENCE

This application claims the benefit of U.S. Provisional Patent Application No. 61/829,131, filed May 30, 2013.

BACKGROUND

An article fabricated on a production line may be inspected for certain features, including defects that might degrade the performance of the article or a system including the article. For example, a hard disk for a hard disk drive may be fabricated on a production line and inspected for certain surface features, including surface and subsurface defects that might degrade the performance of the disk or the hard disk drive. When a surface defect is detected, the article may be deemed unusable and discarded, irrespective of how superficial the defect. In some other instances, articles identified with defects may be salvaged by removing the article from the production line to a separate specialized removal device, to remove defects from the article. However, utilizing a separate specialized removal device may be time intensive. That is, it may take up to half a day to remove defects from a single article, and cause further net production delays.

SUMMARY

Provided herein is an apparatus, including a mapping means for generating a map of locations of surface features of an article based on photon-detector signals corresponding to photons scattered from the surface features of the article, and a surface feature manager. The surface manager is configured to locate a predetermined surface feature of the surface features of the article based, at least in part, on the map of the surface features locations, irradiate photons of a first power onto the location of the predetermined surface feature to analyze the predetermined surface feature, and irradiate photons of a second power onto the location of the predetermined surface feature to remove the predetermined surface feature.

These and other features and aspects of the concepts provided herein may be better understood with reference to the following drawings, description, and appended claims.

DESCRIPTION

Before some particular embodiments are described and/or illustrated in greater detail, it should be understood by persons having ordinary skill in the art that the particular embodiments provided herein do not limit the concepts provided herein, as elements in such particular embodiments may vary. It should likewise be understood that a particular embodiment provided herein has elements which may be readily separated from the particular embodiment and optionally combined with or substituted for elements in any of several other embodiments described and/or illustrated herein.

It should also be understood by persons having ordinary skill in the art that the terminology used herein is for the purpose of describing some particular embodiments, and the terminology does not limit the concepts provided herein. Unless indicated otherwise, ordinal numbers (e.g., first, second, third, etc.) are used to distinguish or identify different elements or steps in a group of elements or steps, and do not supply a serial or numerical limitation. For example, "first," "second," and "third" elements or steps need not necessarily appear in that order, and embodiments need not necessarily be limited to the three elements or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

Unless defined otherwise, all technical and scientific terms used herein have the same meaning as commonly understood by persons of ordinary skill in the art.

An article fabricated on a production line may be inspected for certain features, including defects, such as particle and stain contaminations, scratches and/or voids, that may degrade the performance of the article or a system including the article. It is appreciated that without inspecting an article for surface features, a finished surface of an article, such as a hard disk for a hard disk drive, may unknowingly be contaminated. Further, the contamination of the finished surface of an article may lead to scratch formation, debris generation, and/or corruption of the spacing between the hard disk and a read-write head.

Conventionally, when an article is identified with certain features, such as defects, the article may be discarded, irrespective of how superficial the defect. In some instances, rather than discarding the article, the article may be salvaged by removing the defect from the surface of the article. However, conventional mechanisms for removing defects from an article are time consuming and may cause production delays. For example, in order to remove a defect from an article, the article is removed from the production line and placed on a specialized removal device. In order to transfer the article from the production line to the specialized removal device, the article is carefully sealed and handled to prevent further contamination of the article. Then the specialized removal device analyzes the article for defects in its entirety in order to remove defects. That is, as the specialized removal device scans the article and locates a defect, the specialized removal device removes the defect, rather than directly and individually locating and removing the defects. As such, it can be appreciated that removing defects utilizing a separate specialized removal device can be time consuming and burdensome, which may, in some instances, outweigh the benefits of salvaging an article. As a result, many articles with defects are discarded, rather than salvaged, thereby affecting net article production.

As such, in some embodiments described herein, an imaging apparatus is configured to provide an in situ solution to locate, analyze and remove surface features from an article as the article moves through a production line. For instance, an imaging apparatus described herein is configured to image and generate a map of surface feature locations of an article. Once the locations are determined, a surface feature may be selected for further analysis and/or removal. In some instances described herein, the imaging apparatus includes a surface feature manager that is configured to locate the selected feature based on the location coordinates of the feature from the map, and then irradiate photons onto the selected surface feature for further feature analysis and feature classification. In this way, manufacturing trends leading to certain types of surface features may be identified and corrected, and thereby increase product quality. Further, in some instances described herein, the surface feature manager may irradiate photons of a sufficient power to remove the selected feature from the surface of the article. As such, the imaging apparatus described herein provides a mechanism to utilize a single apparatus to efficiently and rapidly image, locate, analyze and remove features to salvage an article that would otherwise be discarded.

Figure 1:
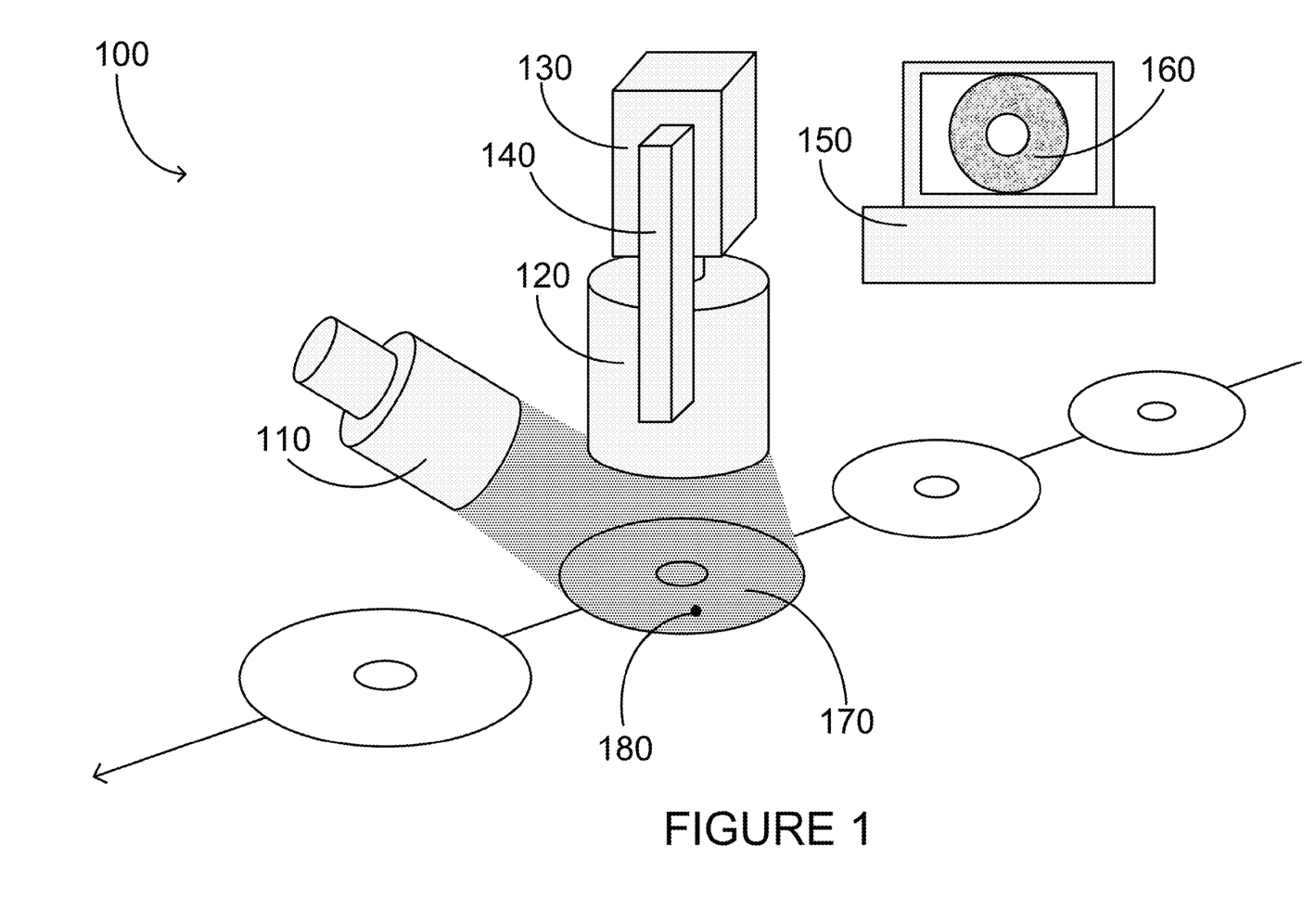
FIG. 1 shows an apparatus configured for surface feature detection and inspection of articles according to one aspect of the present embodiments.

FIG. 1 shows an apparatus configured for surface feature detection and inspection of articles according to one aspect of the present embodiments. Described in greater detail below, the apparatus 100 includes, but is not limited to, a photon emitter 110, an optical setup 120, a camera 130, a surface feature manager 140, and a computer 150 displaying an image 160 of article 170. It is appreciated that the apparatus described herein is illustrative and is not intended to limit the scope of the inventive concepts.

In some embodiments, detection and inspection of features of the article 170 may be performed by directing photons from photon emitter 110 onto the surface of the article 170. When photons scatter from a location of a surface feature, such as surface feature 180, of the article 170, the optical setup 120 detects the scattered photons. The article 170 is imaged by the camera 130, locations of the surface features of the article 170 are mapped, and the locations of the surface features can be represented on image 160. Then, a surface feature, such as surface feature 180, may selected for a deeper feature analysis and/or removal, which is described in greater detail below in FIGS. 6A-6C.

Before proceeding to further describe the various components of apparatus 100, it is appreciated that the article 170 as described herein may be, but is not limited to, semiconductor wafers, magnetic recording media (e.g., hard disks for hard disk drives), glass blanks, workpieces having one or more optically smooth surfaces, and/or workpieces in any stage of manufacture.

It is further appreciated that that the illustration of a single surface feature 180 on the surface of article 170 is illustrative, and is not intended to limit the scope of the inventive concepts described herein. In some embodiments, an article may have no surface features, and in other embodiments the article may have more than one surface feature. It is further appreciated that the size of the surface feature 180 is illustrative, and is not intended to limit the scope of the inventive concepts described herein. It is appreciated that the size of the surface feature on the surface of article 170 may be of any size, such as nanometer-sized, micrometer-sized, etc.

Referring now to photon emitter 110, in some embodiments photon emitter 110 is configured to emit photons onto the entire or onto a portion of the surface of article 170. In some instances, the photon emitter 110 may emit light onto the surface of the article 170 to image and map locations of surface features. For example, the photon emitter 110 may emit white light, blue light, UV light, coherent light, incoherent light, polarized light, non-polarized light, or some combination thereof. As the photon emitter 110 emits photons and/or light onto the surface of the article 170, the photons or light may reflect and/or scatter from the surface of the article 170 and may be captured by the optical setup 120 and the camera 130.

In some embodiments, the photon emitter 110 may emit photons onto the entire surface as illustrated in FIG. 1, or some predetermined portion of the article's surface (e.g., for gradational rotation of the article for piecewise inspection, if desired). In some embodiments, it may be desirable to increase the number of photons (e.g., photon flux density) emitted from the photon emitter 110 to provide an increase in photons scattered for detecting, mapping, and/or characterizing surface features of articles. Such an increase in photon flux density may be with respect to unit time for increased photon power, or with respect to unit area.

It is further appreciated that the angle and position of the photon emitter 110 illustrated in FIG. 1 is illustrative and is not intended to limit the scope of the embodiments. It is appreciated that the photon emitter 110 may be positioned at any location around article 170. It is further appreciated that the angle of the photon emitter 110 may be adjusted to emit photons onto the surface of an article to further detect and inspect specific surface features of the article known to scatter at those specific angles. The angle and position of the photon emitter 110 may also be adjusted to irradiate the entire surface or a predetermined portion of an article.

It is appreciated that the illustration of a single photon emitter is an example, and is not intended to limit the scope of the inventive concepts described herein. In some embodiments, it is appreciated that more than one photon emitter may be utilized to irradiate the surface of an article.

In some embodiments, the apparatus 100 includes an optical setup 120. The optical setup 120, in some embodiments, may be configured to manipulate photons emitted from the photon emitter 110, reflected from the surface of the article 170 and/or scattered from the surface features, such as surface feature 180, of the article 170. For example, the optical setup 120 may include, but is not limited to, lenses, filters, gratings, and mirrors (not shown for purposes of clarity).

For instance, the optical setup 120 may include a lens coupled to a photon detector array (e.g., photon detector array 202 of FIG. 2) of the camera 130 configured to collect and detect images of the surface features of the article 170. In this instance, the lens may have an entrance pupil and an exit pupil, and additional optical components (e.g., other lenses, gratings, and mirrors) may be positioned at or near the entrance pupil of the lens, at or near the exit pupil of the lens (e.g., in-between the exit pupil of the lens and the photon detector array), or some combination thereof to manipulate photons scattered from the surface features of the article 170. In some instances, the lens may be an objective lens, such as a telecentric lens, including an object-space telecentric lens (e.g., entrance pupil at infinity), an image-space telecentric lens (e.g., exit pupil at infinity), or a double telecentric lens (e.g., both pupils at infinity). Coupling a telecentric lens to a photon detector array reduces errors with respect to the mapped position of surface features of articles, reduces distortion of surface features of articles, and/or enables quantitative analysis of photons scattered from surface features of articles, which quantitative analysis includes integration of photon scattering intensity distribution for size determination of surface features of articles. It is appreciated that the optical setup 120 may include more than one lens.

In some embodiments, the optical setup 120 may include filters (not shown), such as wavelength filters, band-pass filters, polarization filters, coherence filters, periodic array-tuned filters, and phase filters. It is appreciated that one or more of these filters may be used to manipulate photons scattered from the surface features of the article 170 to distinguish between different types of surface features. In some embodiments, external filters, such as a band-pass filter, a periodic array-tuned filter, and/or a phase filter, may be used in conjunction with the photon emitter 110 to manipulate photons emitted from the photon emitter 110 prior to reaching the surface of the article 170. For example, a phase filter or waveplate may be used in conjunction with the photon emitter 110 to emit photons onto the surface of the article 170 to distinguish between surface features known to differentially scatter photons with respect to phase. In another example, a wavelength filter may be used to distinguish between surface features known to differentially scatter photons with respect to wavelength, a polarization filter may be used to distinguish between surface features known to differentially scatter photons with respect to polarization, and/or a coherence filter may be used to distinguish between surface features known to differentially scatter photons with respect to coherence.

In some embodiments, the optical setup 120 may include reflective surfaces, such as mirrors. For example, the mirrors may be optical-grade mirror and/or one-way mirrors. In some embodiments, the mirrors may be used to manipulate photons reflected from the surface of the article 170, photons scattered from surface features of the article 170, and/or some combination thereof. In some embodiments, external mirrors may be used in apparatus 100 to manipulate photons emitted from the photon emitter 110. For example, mirrors may be positioned in the apparatus 100 to redirect photons reflected off the surface of the article 170 back onto the surface of the article 170, thereby recycling photons that would otherwise be lost to the environment and minimizing the loss of the intensity of the photons irradiated onto the surface of the article 170.

In some embodiments, the apparatus includes the camera 130 coupled to the optical setup 120 and communicatively coupled (not shown) to the computer 150. In some embodiments, the camera 130 may be configured to record images of the article 170 and transmit the recorded images to the computer 150 for processing and storage. The camera 130 may be a complementary metal-oxide semiconductor ("CMOS") camera, a scientific complementary metal-oxide semiconductor ("sCMOS") camera, a charge-coupled device ("CCD") camera, an electron-multiplying CCD ("EMCDD") camera, or a camera configured for use in feature detection and identification.

In some embodiments, the camera 130 may include a photon detector array (e.g., photon detector array 202 of FIG. 2) configured to collect and detect photons scattered from features on the surface of the article 170. The photon detector array (e.g., photon detector array 202 of FIG. 2) may comprise a complementary metal-oxide semiconductor ("CMOS"), a scientific complementary metal-oxide semiconductor ("sCMOS"), a charge-coupled device ("CCD"), or an electron-multiplying CCD ("EMCDD"), which may be part of the camera 130.

In some embodiments, depending upon factors that may include the type of article, the type of surface features (e.g., particle, stain, scratch, void, etc.), and the like, it may be desirable at times to increase detection time of the photon detector array (e.g., photon detector array 202 of FIG. 2) of the camera 130 to detect more photons for detecting, mapping, and/or characterizing surface features of articles. In some embodiments, for example, detection time may be increased to detect more photons. In such embodiments, a CCD-based photon detector array, including an electron-multiplying EMCCD may be used to further detect more photons.

In some embodiments, the photon detector array and/or camera 130 may be oriented to collect and detect photons scattered from surface features of the article 170 at an optimized distance and/or an optimized angle for a maximum acceptance of scattered photons from one or more types of surface features. Such an optimized angle may be the angle between a ray (e.g., a photon or light ray) including the center line axis of the photon detector array to the surface of the article 170 and the normal (i.e., a line perpendicular to the surface of the article 170) at the point at which the ray is extended. The optimized angle may be equal to or otherwise include a scatter angle for one or more types of surface features, and the scatter angle may be a different angle than the angle of reflection, which angle of reflection is equal to the angle of incidence. For example, photon detector array and/or the camera 130 may be oriented at an optimized angle ranging from 0° to 90°. Here, an optimized angle of 90° represents orientation of the photon detector array and/or camera 130 at a side of the article 170, an optimized angle of 0° represents orientation of the photon detector array or photon detector array directly above the article 170, as illustrated in FIG. 1.

Although FIG. 1 illustrates a single camera with a single photon detector array, it is intended to be illustrative and is not intended to limit the scope of the inventive concepts described herein. In some embodiments, the apparatus 100 may comprise a plurality of cameras including a plurality of photon detector arrays. In other embodiments, the apparatus 100 may include a plurality of cameras, where each camera includes a single photon detector array. In further embodiments, the apparatus 100 may include a single camera including a plurality of photon detector arrays.

In some embodiments, the apparatus 100 further includes the computer 150. The computer 150 may be communicatively coupled (not shown for clarity of illustration) to the camera 130 to store images of the article 170 recorded by the camera 130. In some embodiments, the computer 150 may be communicatively coupled (not shown for clarity of illustration) to the surface feature manager 140 to transmit location coordinates of a specific surface feature to the surface feature manager 140, and further cause the surface feature manger 140 to irradiate photons onto the specific surface feature for analysis and/or for removal.

In some embodiments, the computer 150 may be communicatively coupled (not shown) to the photon emitter 110 to control how photons are emitted onto the surface of the article 170. In some instances, the computer 150 may be configured to move the photon emitter 110 to a distance and/or an angle optimized for inspecting one or more types of features, switch the photon emitter 110 on and/or off, and/or switch between modes for emitting photons and not emitting photons.

Computer 150 may also be configured to, but is not limited to, mount and unmount the article 170 in the apparatus 100, position the article 170 for illumination and inspection by maintaining the position of the article 170 in the apparatus 100, and/or optionally including gradational rotation of the article 170 for piecewise inspection. In some embodiments, the computer 150 may be configured to insert optical components into the optical setup 130, for example, using a mechanical actuator, position optical components for inspection, adjust optical components (e.g., focus lenses) and/or tune optical components for inspection, and/or remove optical components from the optical setup 120.

In some embodiments, the computer 150 may be further configured to identify features of the article 170, such as disk defects. For instance, the computer 150 may be configured to process photon detector array (e.g., photon detector array 202 of FIG. 2) signals from scattered photons, including pixel interpolation for better accuracy (e.g., 10× better than pixel size) with respect to the position of surface features. In some embodiments, the computer 150 may be configured to synchronize each photon emitter of photon emitter 110 with each pixel sensor (e.g., pixel sensor 204 of FIG. 2) of a photon detector array (e.g., photon detector array 202 of FIG. 2) in accordance with a photon emission-photon detection scheme.

In some instances, the computer 150 may map locations of surface features of articles from photon detector array signals or processed photon detector array signals. For example, the computer 150 may be operable to accurately and/or precisely determine the photon scattering intensity distribution (e.g., FIGS. 5A [bottom] and 5B [bottom]) of a feature on the surface of an article. Such a photon scattering intensity distribution may be used to characterize a surface feature of an article both quantitatively and qualitatively.

As noted above, the computer 150 may quantitatively and/or qualitatively characterize surface features of articles, in some instances. With respect to quantitative characterization of a surface feature of an article, mathematical integration of a photon scattering intensity distribution provides the size (e.g., volume) of the surface feature of the article. Quantitative characterization of a surface feature of an article may further include a determination of surface feature position on the article as described herein. Quantitative characterization may even further include the total number of surface features per article, or the number of surface features per unit area per article, as well as the number of each type of surface feature on the article. Such characterization information may be cataloged across a number of articles and be used to correct manufacturing trends should such features include surface and/or subsurface defects that might degrade the performance of the article.

With respect to qualitative characterization of a surface feature of an article, qualitative characterization may include a determination of the morphology, form, or shape of the surface feature of the article, including whether the surface feature is a particle, a stain, a scratch, or a void, etc., which determination may be effected by, but is not limited to, analysis of photon scattering intensity distributions. Qualitative characterization may further include chemical characterization of surface features known to differentially scatter photons such as, but not limited to, certain oxides, which may have faceted surfaces that differentially and/or directionally scatter photons. Qualitative characterization may even further include distinguishing between surface features known to differentially scatter photons with respect to wavelength, polarization, and/or a phase filter or a waveplate.

In some embodiments, qualitative characterization of one or more surface features of an article may include contrasting photon-scattering information in the effective absence of one of the foregoing filters with photon-scattering information using one or more of the foregoing filters or contrasting a first surface features map produced in the effective absence of one of the foregoing filters with a second surface features map (or a number of surface features maps) produced using one or more of the foregoing filters. Along with quantitative characterization information, such qualitative characterization information may be cataloged across a number of articles and be used to correct manufacturing trends should such features include surface and/or subsurface defects that might degrade the performance of the article.

In some embodiments, the computer 150 may perform deep feature analysis of a specific surface feature. For example, in response to the surface feature manager irradiating photons onto the selected surface feature, such as surface feature 180 and further in response to the optical set-up 120 and camera 130 transmitting photon-detector signals corresponding to photons scattered from the selected surface feature, the computer 150 may perform additional analysis, such as Raman spectroscopy analysis, luminescence measurements, loss spectroscopy analysis, electron spectroscopy analysis, based on the photon-detector signals. In this way, the computer 150 may be used to do a more detailed and extensive analysis of a selected surface feature.

It is appreciated that computer 150 may be a desktop computer, a workstation, a portable device (e.g., a mobile device, a tablet, a laptop, or a smartphone), a server or some computing device that may be configured to store and perform image based feature detection and inspection.

Figure 6A:
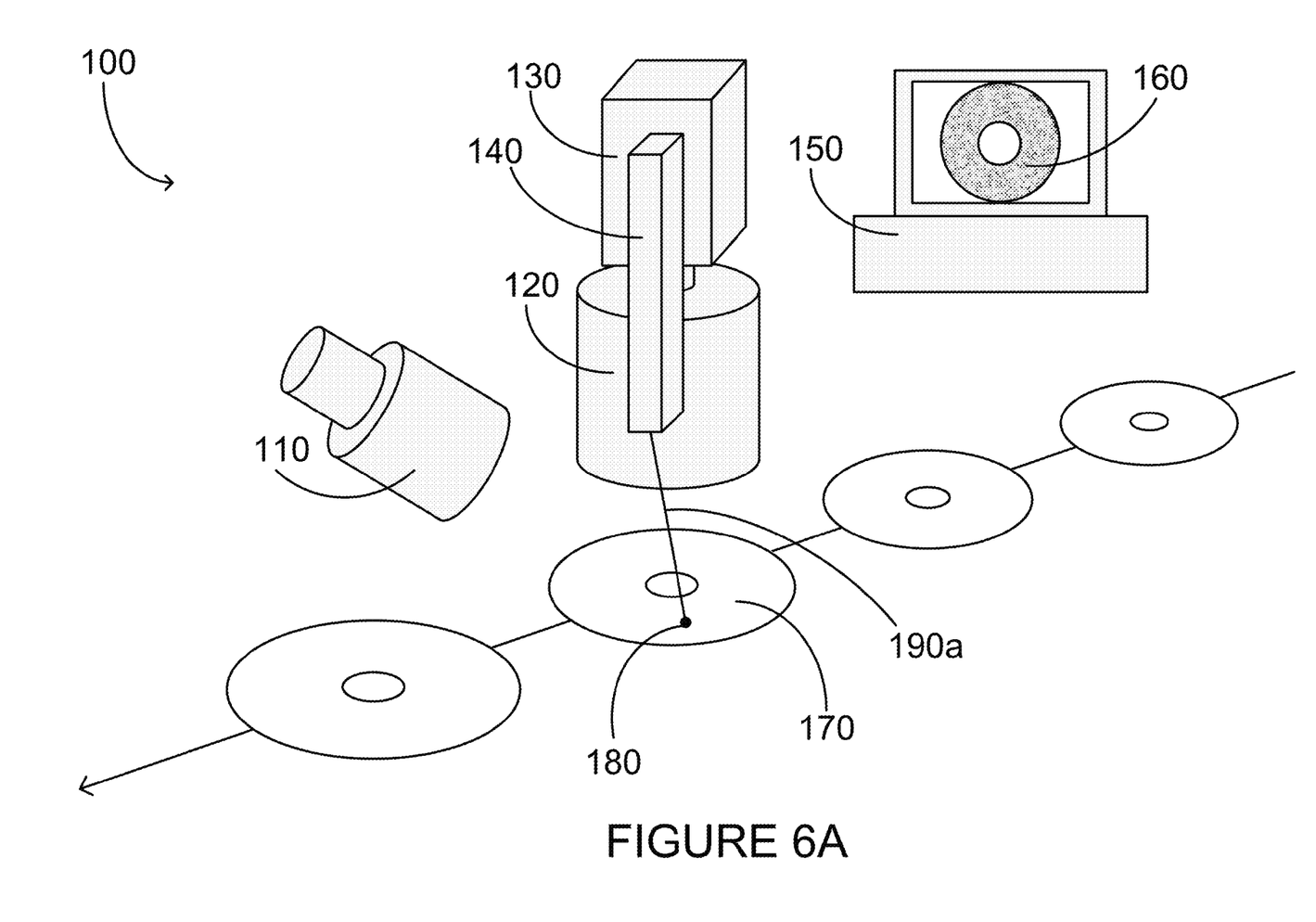
FIG. 6A shows a surface feature manager locating and irradiating photons onto a preselected surface feature of an article according to one aspect of the present embodiments.
Figure 6B:
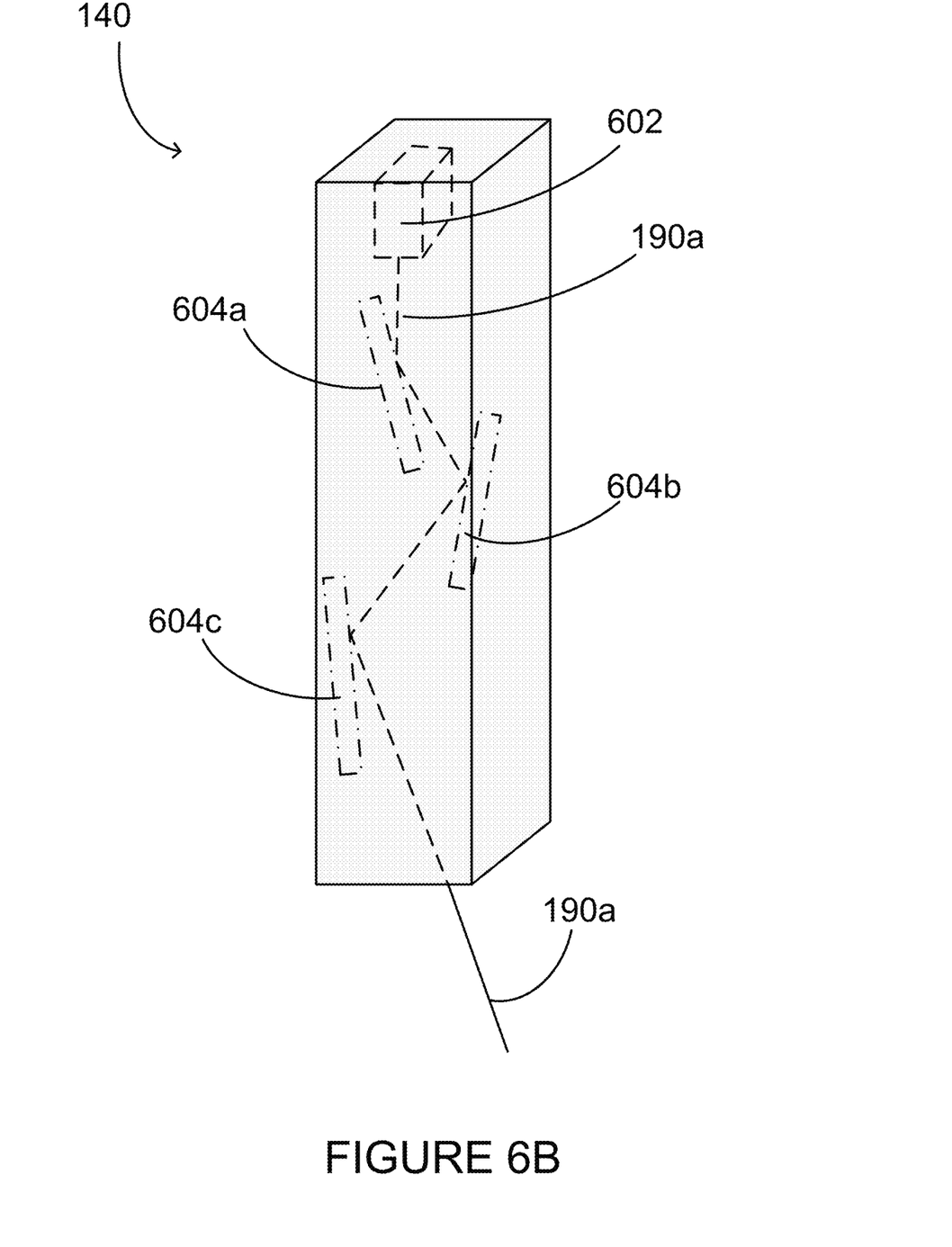
FIG. 6B shows a surface feature manager according to one aspect of the present embodiments.
Figure 6C:
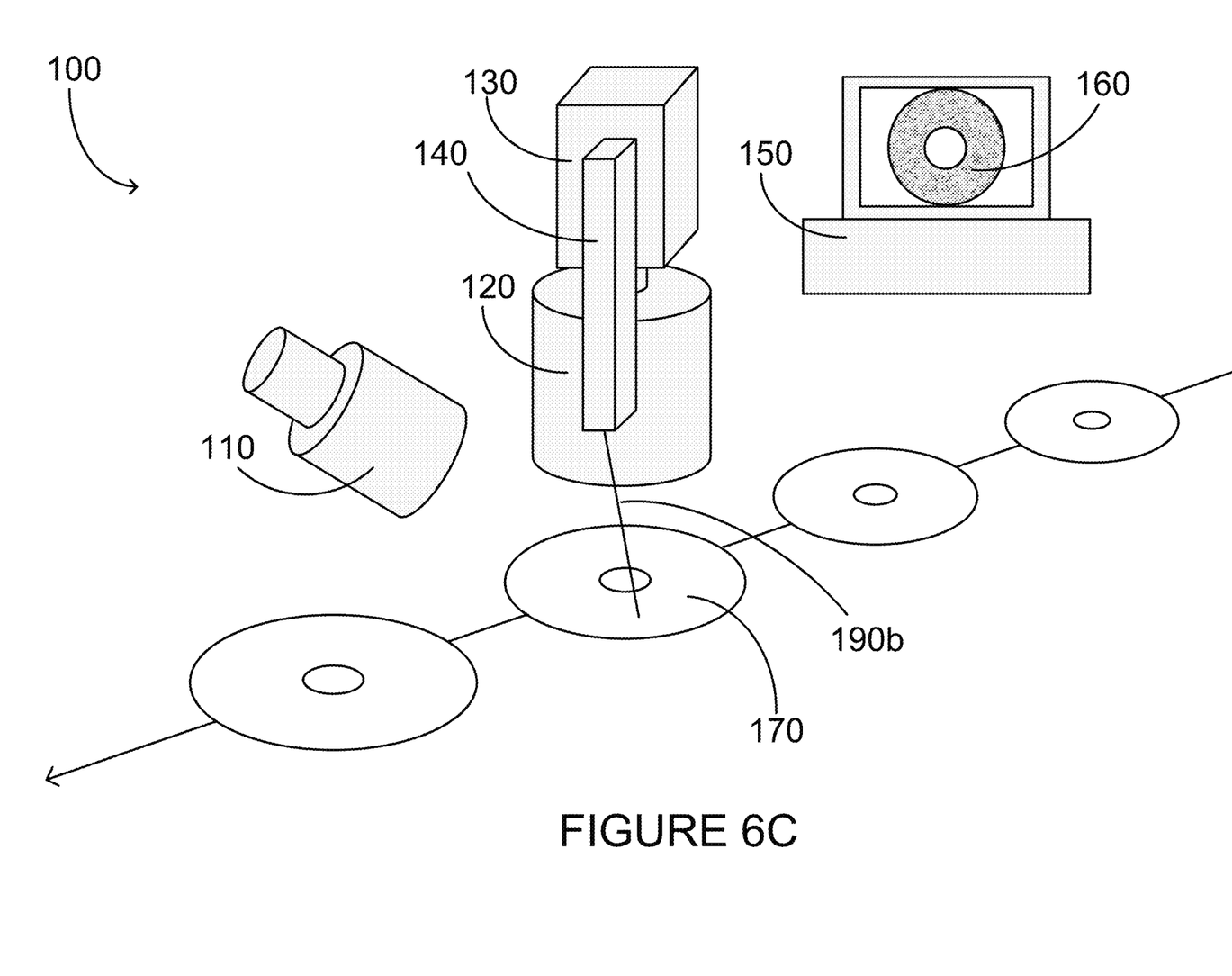
FIG. 6C shows a surface feature manager removing a preselected surface feature from an article according to one aspect of the present embodiments.

In some embodiments, the apparatus 100 further includes a surface feature manager 140. In some embodiments, the surface feature manager 140, which is described in greater detail in FIGS. 6A-6C, is configured to locate a specific surface feature, such as surface feature 180, to irradiate photons onto the surface feature for deep feature analysis. In this way, manufacturing trends leading to certain types of surface features may be identified and corrected, and thereby increase product quality. Further, in some embodiments, the surface feature manager 140 is configured to remove the surface feature 180 from the surface of the article 170. In this way, the apparatus 100 described herein, in some embodiments, provides a mechanism to salvage an article that may have a defect, rather than discarding the article, which results in a higher article production yield compared to other article inspection mechanisms.

It is further appreciated that the apparatus 100 described herein may be configured to process or inspect articles at a rate greater than or commensurate with the rate at which the articles or workpieces thereof are produced. Processing or inspecting articles at rates greater than or commensurate with the rate at which the articles or workpieces thereof are produced is a function of many features of the apparatus 100 described herein, including, but not limited to, photon emitters and/or articles that need not be moved (e.g., for scanning) during processing or inspecting. For example, with photon emitter 110, an article such as a hard disk of a hard disk drive need not be rotated during processing or inspecting. As such, the apparatus 100 can hold an article stationary while emitting photons onto the surface of the article, thereby saving time since the article can be quickly examined while remaining in a static position.

Figure 2:
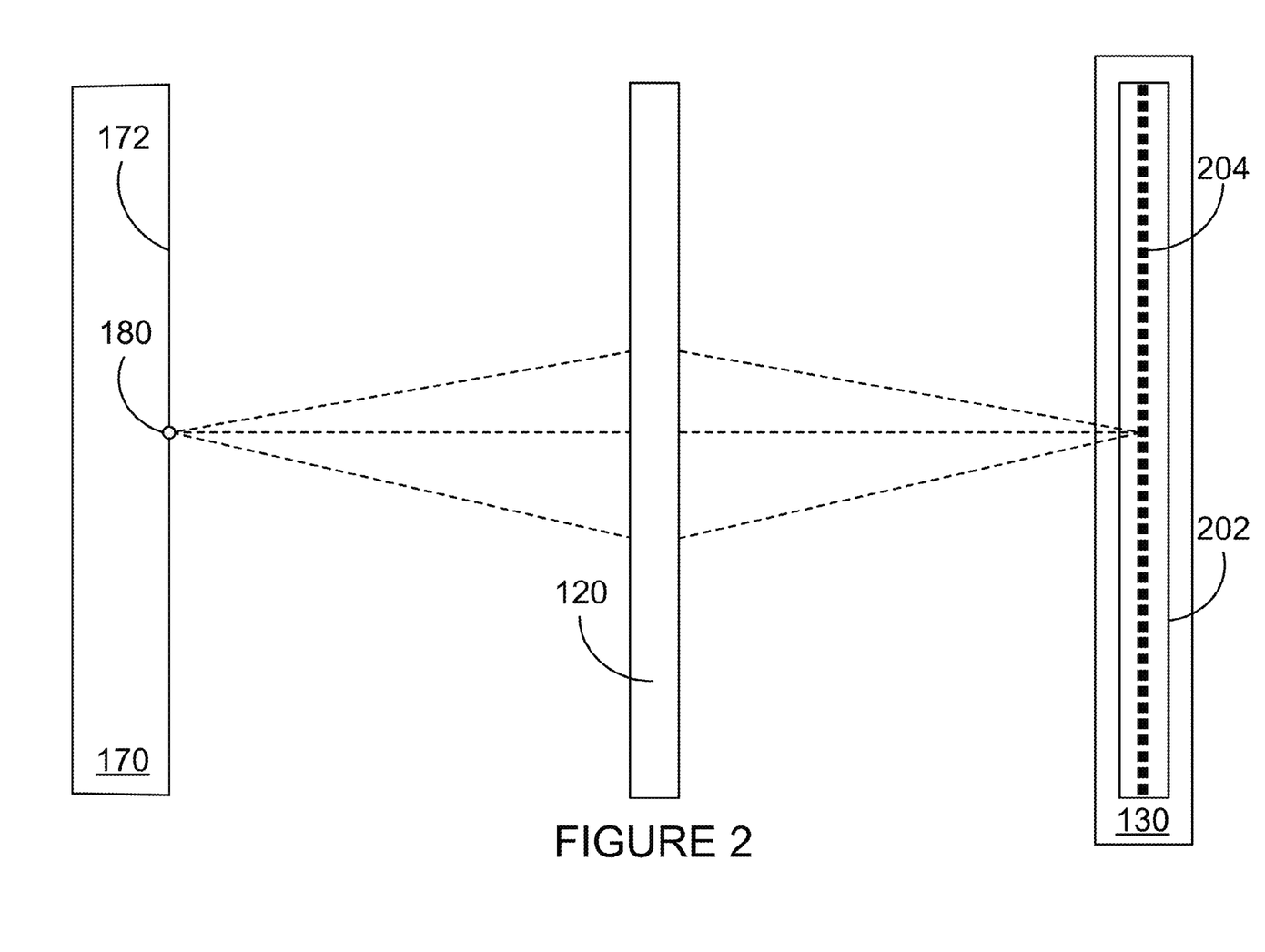
FIG. 2 illustrates a schematic of photons scattering from a surface feature of an article, through an optical setup, and onto a photon detector array according to one aspect of the present embodiments.

Referring now to FIG. 2, a schematic of photons scattering from a surface feature of an article, through an optical set up, and onto a photon detector array is illustrated according to one aspect of the present embodiments. As illustrated in FIG. 2, article 170 comprises a surface 172 and a surface feature 180. Although FIG. 2 illustrates an article with a single surface feature, it is intended to be an example and not intended to limit the scope of the inventive concepts. It is appreciated that an article may have more than one feature, which may be imaged for feature detection, identification, feature analysis, and/or feature removal.

Photons emitted from a photon emitter, such as photon emitter 110 of FIG. 1, or a plurality of photon emitters, may be scattered by the surface feature 180 and collected and detected by the optical setup 120 in combination with photon detector array 202 of camera 130, which may be positioned at a distance and/or an angle for an optimum acceptance of photons (e.g., maximum acceptance of photons with minimum background noise) scattered from one or more types of features.

The optical setup 120, which may comprise a telecentric lens, may collect and focus the photons scattered from the surface feature 180 onto one or more pixel sensors 204 of photon detector array 202, which each may comprise a photon detector coupled to an amplifier (e.g., CMOS/sCMOS-based photon detector array). The one or more pixel sensors 204, each of which corresponds to a particular, fixed area of an article's 170 surface 172 and a pixel in a map of the article's 170 surface features, may provide one or more signals to a computer, such as computer 150 described in FIG. 1, for mapping or otherwise determining the location of the surface feature 180.

Figure 3:
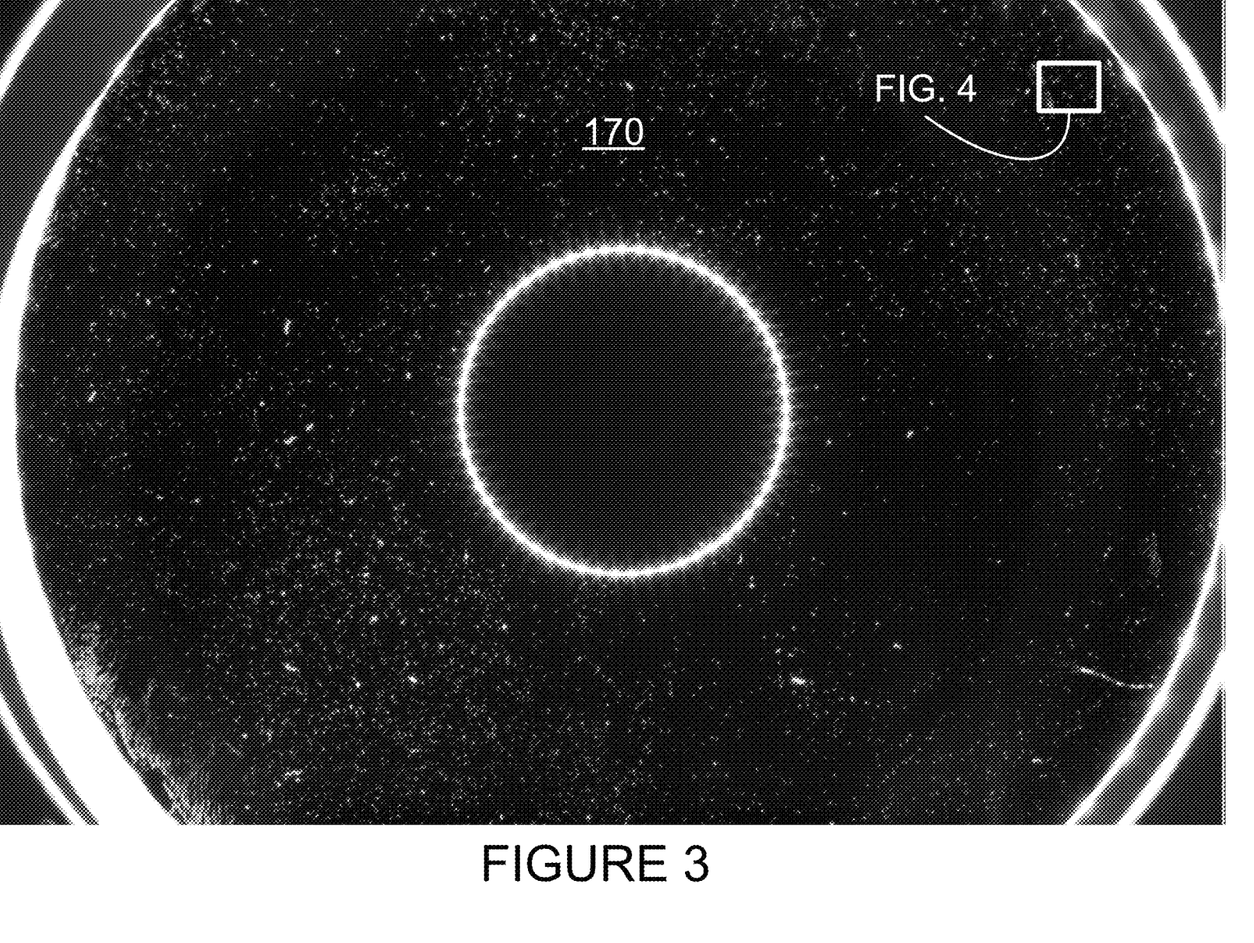
FIG. 3 shows a close-up partial map of surface features of an article inspected for surface features according to one aspect of the present embodiments.
Figure 4:
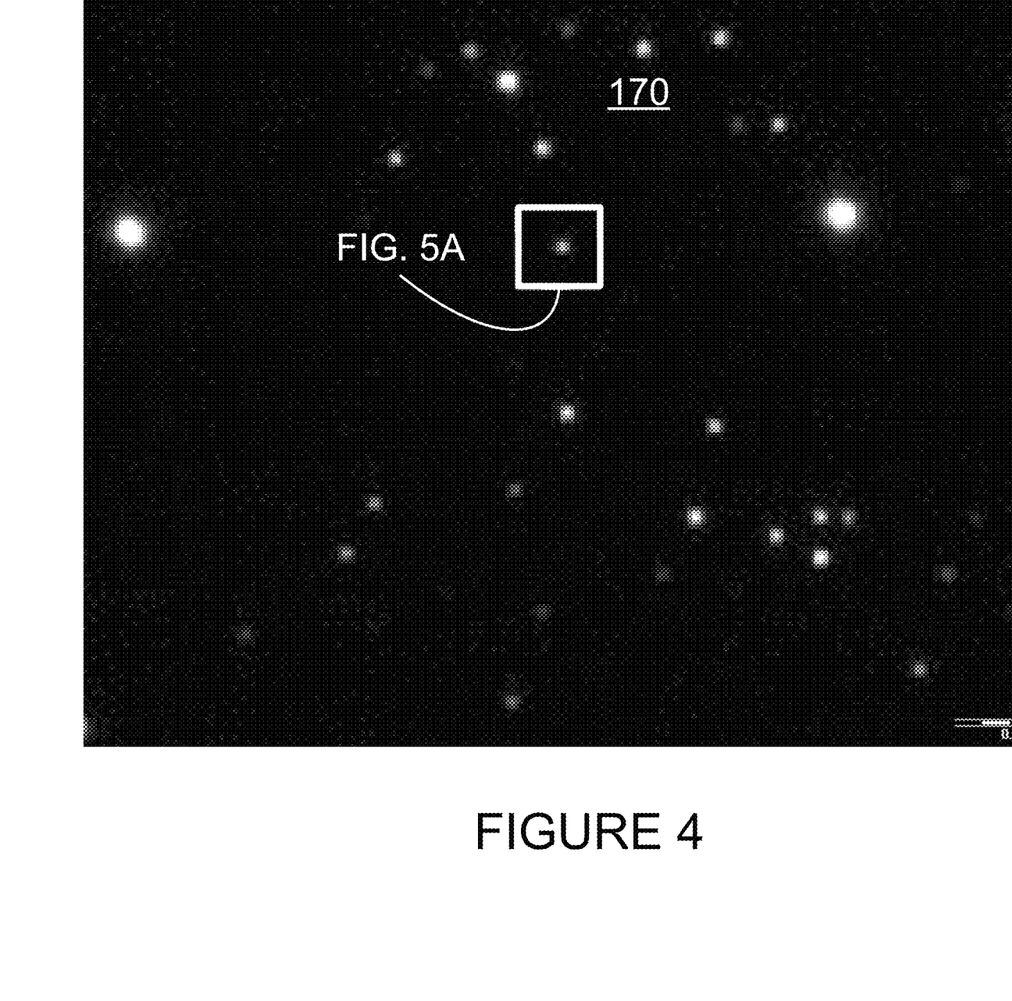
FIG. 4 provides a close-up image of a portion of the surface features map shown in FIG. 3, according to one aspect of the present embodiments.
Figure 5A:
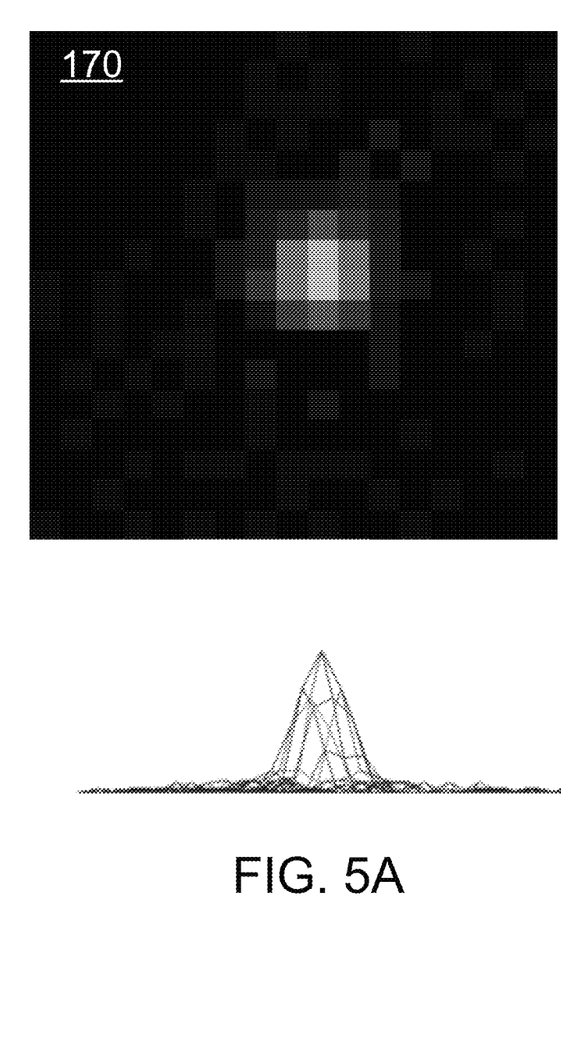
FIG. 5A (top) provides an illustrative example of a close-up image of the corresponding surface feature from the surface features map provided in FIG. 4, and FIG. 5A (bottom) provides a photon scattering intensity distribution of the surface feature, according to aspects of the present embodiments.
Figure 5B:
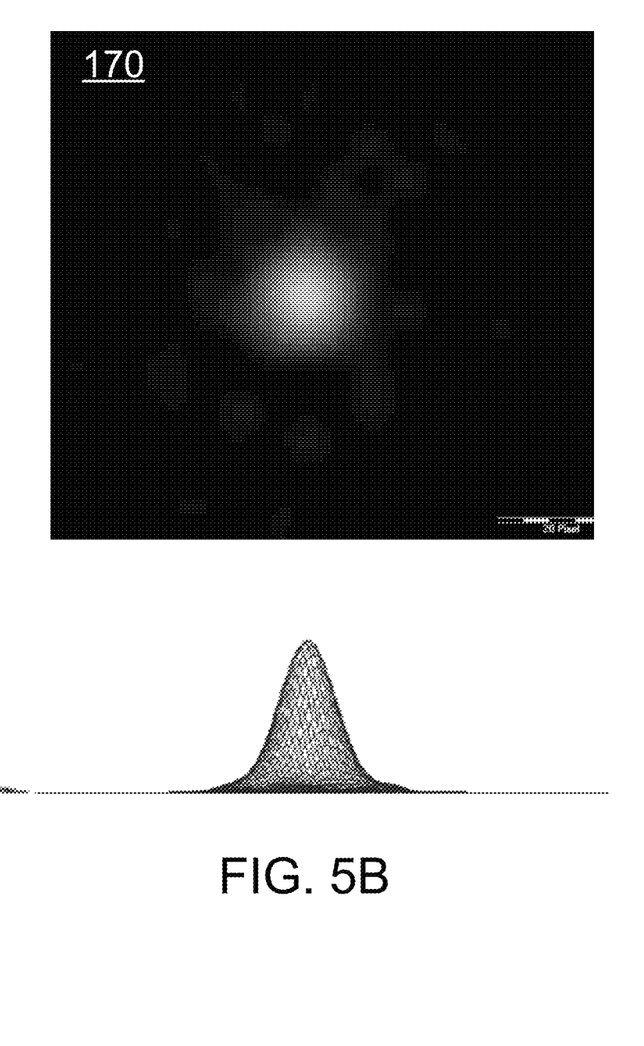
FIG. 5B (top) provides a close-up, pixel-interpolated image of the surface feature depicted in FIG. 5A, and FIG. 5B (bottom) provides a photon scattering intensity distribution of the pixel-interpolated surface feature, according to aspects of the present embodiments.

FIG. 5A (top) provides an illustrative example of a feature in a close-up image of a portion of the map of surface features provided in FIG. 4, which, in turn, is an illustrative example of a close-up image of a portion of the map of surface features provided in FIG. 3. A computer, such as computer 150 of FIG. 1, or equivalent device, may subsequently use pixel interpolation, FIG. 5A (bottom), for further mapping the surface feature. FIG. 5B provides an illustrative example of a pixel-interpolated image of a surface feature, such as the surface feature from FIG. 5A.

Although FIGS. 3-4 and FIGS. 5A-5B depict images of a magnetic medium, it is appreciated that the depictions are illustrative and are not intended to limit the scope of the inventive concepts described herein. It is appreciated that the imaging, mapping, and pixel interpolation as illustrated in FIGS. 3-4 and FIGS. 5A-5B may be used for articles in different stages of manufacture.

Referring now to FIG. 6A, a surface feature manager 140 is shown locating and irradiating photons 190a onto a preselected surface feature of an article according to one aspect of the present embodiments. In some embodiments, the surface feature manager locates a specific surface feature based on a map of surface feature locations of article 170 generated by computer 150. In some embodiments, the computer 150 generates a map of article 170 based on an x-axis and y-axis coordinate system. In this exemplary embodiment, the x-axis and the y-axis may refer to longitudinal and latitudinal directions, respectively, with reference to article 170.

After the computer 150 generates the map, a surface feature may be selected for deep feature analysis. In some embodiments, a surface feature may be automatically selected and/or selected based on a user selection. In this exemplary embodiment, surface feature 180 is selected for deep feature analysis, and the computer 150 transmits the location coordinates (e.g., x-axis and y-axis coordinates) of surface feature 180 to the surface feature manager 140.

The surface feature manager 140 locates the surface feature 180 based on the location coordinates, and irradiates photons onto the surface feature 180. In some embodiments, the surface feature manager 140 includes a photon source 602 (FIG. 6B) that emits photons, and reflective surfaces 604a-604c, such as mirrors, that direct the photons emitted from the photon source onto surface feature 180, as illustrated in FIG. 6B. When the surface feature manager 140 receives the location coordinates of the surface feature 180, the reflective surfaces 604a, 604b, and 604c may be tilted and/or pivoted about x-axis and/or y-axis directions to cause the emitted photons 190a (FIG. 6A) to irradiate the surface feature 180, as shown in FIG. 6A.

In some embodiments, once the photons 190a are directed onto the surface feature 180, the surface feature 180 may further analyzed. In some instances, the photons 190a irradiated onto the surface feature 180 may be of a low power sufficient to irradiate the surface feature 180 for analyzing the surface feature 180. For example, the surface feature manager 140 may emit collimated light, such as a laser beam, onto the surface feature 180, that causes the laser beam to scatter off the surface feature 180. As noted in FIG. 1, the laser beams scattered from the surface feature 180 are captured by the optical setup 120 and/or the photon detector array (e.g., photon detector array 202 of FIG. 2) of camera 130, and then photon-detector signals are transmitted to the computer 150 to analyze and process the photon-detector signals. In this exemplary embodiment, based on the photon-detector signals, the computer 150 may perform a Raman spectroscopy analysis of the surface feature 180, luminescence measurements, and/or perform qualitative and/or quantitative characterization of the surface feature 180 as described herein.

In some embodiments, rather than irradiating collimated light onto the surface feature 180, the surface feature manager 140 may irradiate an electron beam, an ion beam, and/or X-rays onto the surface feature 180. It is appreciated that by irradiating the surface feature 180 with aforementioned sources, the surface feature 180 may react differently to each source and allow for different types of analysis of the surface feature 180. That is, the surface feature 180 may react differently to an electron beam irradiated upon it compared to an ion beam and further differently compared to X-rays, which may reveal different types of information. Based on the surface feature's 180 reaction to a specific type of source, different types of analysis may be performed. For instance, computer 150 may perform loss spectroscopy analysis and/or electron spectroscopy analysis when an electron beam is irradiated onto the surface feature 180.

In some embodiments, the surface feature manager 140 may be configured to irradiated a different combination of collimated light, electron beam, ion beam, and X-rays. In this exemplary embodiment, it is appreciated that different combination analyses of a surface feature may be performed, such as Raman spectroscopy analysis, luminescence measurements, loss spectroscopy analysis, electron spectroscopy analysis, and/or some combination thereof based on the source type irradiating the surface feature 180.

It is further appreciated that the combination of the surface feature manager 140, the camera 130, optical set-up 120 and the computer 150 allows for nearly real-time deep analysis of a specific surface feature while the article is moving through a production line. It is also appreciated that the apparatus 100 provides the convenience and certain time efficiencies by performing targeted deep analysis of individual surface features without utilizing a separate specialized removal device and further without removing the article from a production line.

Referring now to FIG. 6C, a surface feature manager removing a preselected surface feature from an article is shown according to one aspect of the present embodiments. In some embodiments, rather than discarding an article with a certain surface feature, such as a defect, the surface feature manager is used to salvage the article by irradiating photons to remove a specific surface feature. After the surface feature manager 140 receives location coordinates of surface feature 180 (such as described in FIG. 6A), the surface feature manager 140 locates the position of surface feature 180, and then irradiates collimated light 190b (FIG. 6C), such as a laser beam, of sufficient power to cause the surface feature 180 to evaporate or to slice off the surface of the article 170. It is appreciated that by removing defects from the surface of an article, more useable articles are produced in comparison to articles produced by conventional inspection apparatus.

It is further appreciated that because apparatus 100 provides a combined mechanism to locate, analyze, and remove surface features from an article, certain efficiencies are gained as described herein. For instance, the apparatus 100 allows for nearly real-time identification and location of defects on the surface of an article, and provides a nearly real-time solution to the problem (e.g., removal of the defect) in contrast to conventional mechanisms that are cumbersome and time intensive. Moreover, the apparatus 100 provides a mechanism to do more targeted analysis and/or removal of individual surface features, which provides additional efficiencies in article production.

As such, provided herein is an apparatus, including: a photon emitter configured to emit photons onto a surface of an article, a photon detector configured to receive photons scattered from surface features of the article, a mapping means for generating a map of the locations of surface features of the article based on information received from the photon detector, and a surface feature manager configured to utilize, at least in part, the map of the surface feature locations to locate and irradiate photons specifically onto a surface feature preselected from the mapped surface features.

In some embodiments, the preselected surface feature is a single surface feature of the article. In some embodiments, the surface feature manager includes one or more reflective surfaces configured to controllably direct the irradiating photons to the location of the preselected surface feature. In some embodiments, the mapping means transmits location coordinates of the preselected surface feature to the surface feature manager, and the surface feature manager locates the preselected surface feature based on the location coordinates received from the mapping means.

In some embodiments, the photon detector is further configured to receive the irradiating photons scattered from the preselected surface feature, and the mapping means is further configured to analyze and classify the preselected surface feature based on information received from the photon detector. The surface feature manager is further configured to remove the preselected surface feature, in some embodiments. In some embodiments, the apparatus further includes a telecentric lens coupled to the photon detector. In some embodiments, the photon detector includes a complementary metal-oxide semiconductor ("CMOS"), a scientific complementary metal-oxide semiconductor ("sCMOS"), or a charge-coupled device ("CCD").

Also provided herein is an apparatus including a mapping means for generating a map of locations of surface features of an article based on photon-detector signals corresponding to photons scattered from the surface features of the article, and a surface feature manager. In some embodiments, the surface feature manager is configured to: locate a predetermined surface feature of the surface features of the article based, at least in part, on the map of the surface features locations, irradiate photons of a first power onto the location of the predetermined surface feature to analyze the predetermined surface feature, and irradiate photons of a second power onto the location of the predetermined surface feature to remove the predetermined surface feature.

In some embodiments, the first and second power are different. In some embodiments, the surface feature manager includes one or more reflective surfaces configured to controllably direct the irradiating photons to the location of the preselected surface feature. In some embodiments, the mapping means transmits location coordinates of the preselected surface feature to the surface feature manager, and the surface feature manager locates the preselected surface feature based on the location coordinates received from the mapping means. In some embodiments, the apparatus further includes a photon detector configured to receive photons scattered from surface features of the article and transmit photon-detector signals to the mapping means.

Also provided herein is an apparatus including a processing means configured to select, for removal, a surface feature from a surface features map of surface features of an article, wherein the surface features map includes location coordinates of the surface features of the article based on photon-detector signals corresponding to photons scattered from the surface features. In some embodiments, the apparatus further includes a surface feature manager configured to locate the selected surface feature based on the location coordinates of the selected surface feature received from the processing means, and irradiate photons onto the selected surface feature to remove the selected surface feature from the article.

In some embodiments, the surface feature manager includes one or more reflective surfaces configured to controllably direct the irradiating photons to the location of the preselected surface feature. The surface feature manager is configured, in some embodiments, to irradiate photons onto the location of the selected surface feature to analyze the selected surface feature prior to irradiating photons to remove the selected surface feature. In some embodiments, the surface feature manager is configured to irradiate photons of a first power onto the location of the selected surface feature to analyze the selected surface feature, and the surface feature manager irradiates photons of a second power to remove the selected surface feature. The first and second powers are different, in some embodiments.

In some embodiments, the apparatus further includes a photon detector configured to receive photons scattered from surface features of the article and transmit photon-detector signals to the processing means. In some embodiments, the photon detector includes a complementary metal-oxide semiconductor ("CMOS"), a scientific complementary metal-oxide semiconductor ("sCMOS"), or a charge-coupled device ("CCD").

While some particular embodiments have been described and/or illustrated herein, and while these particular embodiments have been described and/or illustrated in considerable detail, it is not the intention of the applicants for these particular embodiments to limit the scope of the concepts presented herein. Additional adaptations and/or modifications may readily appear to persons having ordinary skill in the art, and, in broader aspects, these adaptations and/or modifications may be encompassed as well. Accordingly, departures may be made from the foregoing embodiments without departing from the scope of the concepts provided herein. The implementations provided herein and other implementations are within the scope of the following claims.

What is claimed is:

1. An apparatus comprising:
a photon emitter configured to emit photons onto a surface of an article;
a photon detector configured to receive photons scattered from surface features of the article;
mirrors configured to redirect photons reflected off the surface of the article back onto the surface of the article to recycle photons;
a mapping means for generating a map of locations of surface features of the article based on information received from the photon detector; and
a surface feature manager configured to utilize, at least in part, the map of the surface feature locations to locate and irradiate photons onto a surface feature preselected from the mapped surface features,
wherein the photon detector is further configured to receive the irradiating photons scattered from the preselected surface feature.

2. The apparatus of claim 1, wherein the preselected surface feature is a single surface feature of the article.

3. The apparatus of claim 1, wherein the surface feature manager includes one or more reflective surfaces configured to controllably direct the irradiating photons to the location of the preselected surface feature.

4. The apparatus of claim 1, wherein:
the mapping means transmits location coordinates of the preselected surface feature to the surface feature manager; and
the surface feature manager locates the preselected surface feature based on the location coordinates received from the mapping means.

5. The apparatus of claim 1, wherein
the mapping means is further configured to analyze and classify the preselected surface feature based on information received from the photon detector.

6. The apparatus of claim 1, wherein the surface feature manager is further configured to remove the preselected surface feature.

7. The apparatus of claim 1 further comprising a telecentric lens coupled to the photon detector.

8. The apparatus of claim 1, wherein the photon detector comprises a complementary metal-oxide semiconductor ("CMOS"), a scientific complementary metal-oxide semiconductor ("sCMOS"), or a charge-coupled device ("CCD").

9. An apparatus comprising:
a photon emitter configured to emit photons onto a surface of an article;
a mapping means for generating a map of locations of surface features of the article based on photon-detector signals corresponding to photons emitted from the photon emitter that are scattered from the surface features of the article, wherein the photon emitter is synchronized with a photon-detector; and
a surface feature manager configured to:
locate a predetermined surface feature of the surface features of the article based, at least in part, on the map of the surface features locations,
irradiate photons of a first power onto the location of the predetermined surface feature to analyze the predetermined surface feature, and
irradiate photons of a second power onto the location of the predetermined surface feature to remove the predetermined surface feature.

10. The apparatus of claim 9, wherein the first and second powers are different.

11. The apparatus of claim 9, wherein the surface feature manager includes one or more reflective surfaces configured to controllably direct the irradiating photons to the location of the preselected surface feature.

12. The apparatus of claim 9, wherein:
the mapping means transmits location coordinates of the preselected surface feature to the surface feature manager; and
the surface feature manager locates the preselected surface feature based on the location coordinates received from the mapping means.

13. The apparatus of claim 9 further comprising the photon detector configured to receive the photons emitted from the photon emitter that are scattered from the surface features of the article and transmit photon-detector signals to the mapping means.

14. An apparatus comprising:
a photon emitter configured to emit photons onto a surface of an article;
a processing means configured to select, for removal, a surface feature from a surface features map of surface features of an article, wherein the surface features map includes location coordinates of the surface features of the article based on photon-detector signals corresponding to photons scattered from the surface features, and wherein the processing means is further configured to determine chemical characterization associated with the surface features; and
a surface feature manager configured to:
locate a selected surface feature based on the location coordinates of the selected surface feature received from the processing means,
irradiate photons onto a location of the selected surface feature to analyze the selected surface feature, and
irradiate photons onto the selected surface feature to remove the selected surface feature from the article.

15. The apparatus of claim 14, wherein the surface feature manager includes one or more reflective surfaces configured to controllably direct the irradiating photons to the location of the preselected surface feature.

16. The apparatus of claim 14, wherein the surface feature manager is further configured to irradiate photons onto the location of the selected surface feature to analyze the selected surface feature prior to irradiating photons to remove the selected surface feature.

17. The apparatus of claim 14, wherein:
the surface feature manager is further configured to irradiate photons of a first power onto the location of the selected surface feature to analyze the selected surface feature; and
the surface feature manager is further configured to irradiate photons of a second power to remove the selected surface feature.

18. The apparatus of claim 17, wherein the first and second powers are different.

19. The apparatus of claim 14 further comprising a photon detector configured to receive photons scattered from surface features of the article and transmit photon-detector signals to the processing means.

20. The apparatus of claim 19, wherein the photon detector comprises a complementary metal-oxide semiconductor ("CMOS"), a scientific complementary metal-oxide semiconductor ("sCMOS"), or a charge-coupled device ("CCD").

* * * * *